United States Patent
Elghazzawi et al.

(10) Patent No.: US 11,980,767 B2
(45) Date of Patent: May 14, 2024

(54) MEDICAL EQUIPMENT MESSAGING

(71) Applicant: ZOLL Medical Corporation, Chelmsford, MA (US)

(72) Inventors: Ziad F Elghazzawi, Newton, MA (US); C. Shane Reid, Boulder, CO (US); Andrew D Funk, Boulder, CO (US); Robert H Gotschall, Thornton, CO (US); Charles E Sawyer, Jr., Sudbury, MA (US); Melissa M Dascoli, Wakefield, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 321 days.

(21) Appl. No.: 16/208,813

(22) Filed: Dec. 4, 2018

(65) Prior Publication Data

US 2019/0099608 A1  Apr. 4, 2019

Related U.S. Application Data

(63) Continuation of application No. 15/046,671, filed on Feb. 18, 2016, now abandoned, which is a
(Continued)

(51) Int. Cl.
*A61N 1/39* (2006.01)
*A61N 1/372* (2006.01)

(52) U.S. Cl.
CPC ....... *A61N 1/3993* (2013.01); *A61N 1/37247* (2013.01); *A61N 1/37282* (2013.01)

(58) Field of Classification Search
None
See application file for complete search history.

(56) References Cited

U.S. PATENT DOCUMENTS 5,700,281 A  12/1997  Brewer et al.
6,321,113 B1  11/2001  Parker et al.
(Continued)

OTHER PUBLICATIONS

Wikipedia, "SIM card," accessed Feb. 19, 2021, https://en.wikipedia.org/wiki/SIM_card (Year: 2021).*
(Continued)

*Primary Examiner* — Michael W Kahelin
(74) *Attorney, Agent, or Firm* — ZOLL Medical Corporation

(57) ABSTRACT

A medical device management system comprising a defibrillating apparatus, which comprises a plurality of electrodes configured to monitor ECG signals and deliver a defibrillation shock. The system including a communication unit configured to establish a secured wireless network, automatically generate a first text message upon receipt of a signal indicative of deployment of the defibrillating apparatus, associate the first text message with a unit identifier, automatically send the first text message, automatically generate a second text message comprising defibrillation shock status upon delivery of the defibrillation shock, associate the second text message with the unit identifier, automatically send the second text message; and a handheld device associated with a caregiver and configured to receive the first and second text messages and associate the first and second text messages with the specific defibrillating apparatus based on the unit identifier specific to the defibrillating apparatus.

28 Claims, 7 Drawing Sheets

Related U.S. Application Data continuation of application No. 13/560,035, filed on Jul. 27, 2012, now Pat. No. 9,295,849.

(56) References Cited

U.S. PATENT DOCUMENTS

| | | | |
|---|---|---|---|
| 7,027,870 B2 | 4/2006 | Limousin et al. | |
| 7,728,548 B2 | 6/2010 | Daynes et al. | |
| 7,769,465 B2 | 8/2010 | Matos | |
| 7,840,277 B2 | 11/2010 | Matos | |
| 2003/0025602 A1* | 2/2003 | Medema | G16H 40/20 340/568.1 |
| 2003/0212311 A1* | 11/2003 | Nova | A61N 1/37258 600/300 |
| 2003/0233129 A1* | 12/2003 | Matos | A61B 5/411 607/5 |
| 2005/0107846 A1 | 5/2005 | Sweeney | |
| 2006/0128404 A1* | 6/2006 | Klassen | H04M 1/72436 455/466 |
| 2007/0213600 A1 | 9/2007 | John et al. | |
| 2009/0058635 A1* | 3/2009 | LaLonde | A61B 5/747 340/539.11 |
| 2009/0292340 A1 | 11/2009 | Mass et al. | |
| 2010/0087173 A1* | 4/2010 | Lin | H04L 51/216 455/412.2 |
| 2010/0241181 A1 | 9/2010 | Savage et al. | |
| 2011/0060378 A1 | 3/2011 | Tuysserkani | |

OTHER PUBLICATIONS

Wikipedia, "MSISDN," accessed Feb. 19, 2021, https://en.wikipedia.org/wiki/MSISDN (Year: 2021).*

International Search Report and Written Opinion, PCT/US2013/043353, dated Aug. 27, 2013, 10 pages.

\* cited by examiner

MEDICAL EQUIPMENT MESSAGING

CROSS-REFERENCE TO RELATED APPLICATIONS

This application is a continuation application and claims priority under 35 U.S.C. § 120 to U.S. patent application Ser. No. 15/046,671, filed on Feb. 18, 2016, which claims benefit to U.S. patent application Ser. No. 13/560,035, filed on Jul. 27, 2012, now U.S. Pat. No. 9,295,849, issued Mar. 29, 2016, which are each incorporated by reference herein in their entirety.

TECHNICAL FIELD

Systems and techniques for providing text-based communications from medical equipment such as automated external defibrillators (AEDs) are described herein.

BACKGROUND

Sudden health problems such as sudden cardiac arrest and injuries caused by accidents kill thousands of people and cause permanent injury every year. Fast and competent care can be essential to positive outcomes in such situations. For example, it is said that the chance of surviving a sudden cardiac arrest falls by ten percent for every minute in delaying effective treatment.

Emergency events like sudden cardiac arrests and accidents are generally responded to by organized emergency response units, such as ambulance or fire crews, and by laypeople who are immediately around the events so that they personally witness or offer assistance for the events.

SUMMARY

In some aspects, a method includes receiving a first signal indicative of deployment of an automated external defibrillator, sending, from the automated external defibrillator, a first text message upon receipt of the first signal indicative of deployment of the automated external defibrillator, receiving a second signal indicative of discharge of the automated external defibrillator, and sending, from the automated external defibrillator, a second text message upon receipt of the second signal indicative of discharge of the automated external defibrillator.

In some additional aspects, a method includes storing a network passcode in a memory associated with the automated external defibrillator, detecting deployment of the automated external defibrillator, upon detection of deployment, establishing a connection with a secured wireless network by accessing stored passcode information for the secured wireless network, and sending one or more text messages, from the automated external defibrillator via the secured wireless network.

In some additional aspects, a method includes performing, by a self-test unit in an automated external defibrillator, a self-test of the automated external defibrillator at regular time-based intervals and sending, from the automated external defibrillator to a server, one or more text messages including information associated with results of the self-test.

Other embodiments of these aspects include corresponding computer systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

Other features and advantages of the invention will be apparent from the drawings, detailed description, and claims.

DETAILED DESCRIPTION

Described herein are systems and techniques for transmitting text messages from a rescue scene to an emergency response dispatch center or medical equipment management center. In general, text messaging is the exchange of brief written text messages between two or more devices over a phone network. Text messaging can be used to provide communications between a piece of medical equipment such as an automated external defibrillator (AED) and an emergency response dispatch center as a substitute for voice calls in situations where voice communication is impossible or undesirable.

In some examples, medical equipment, such as an automated external defibrillator (AED), is configured to establish a wireless connection with a wireless network to enable the medical equipment to send (and optionally receive) text-based messages such as short message service (SMS) or multi-media message service (MMS) messages. For example, the medical equipment can be configured to establish a wireless data connection over a Wi-Fi network and send text messages to an emergency response center (e.g., a 911 center) automatically based on deployment or activation of the medical equipment.

In some examples, described herein are systems and techniques for transmitting text messages from medical equipment, such as an automated external defibrillator (AED), to a medical equipment management system. More particularly, the medical equipment is configured to establish a wireless connection with a wireless network to enable the medical equipment to send (and optionally receive) messages to a remotely located medical equipment management system. For example, the medical equipment can be configured to send text messages to the medical equipment management system automatically based on self-test routines executed on the medical equipment.

In some examples, the medical equipment can include a cellular modem for sending/receiving of text messages. In some additional examples, the medical equipment can be configured to establish a wireless data connection over a Wi-Fi network and send text messages to the medical equipment management system and/or emergency response center via the Wi-Fi network. In some examples, in order to establish the connection with a secured Wi-Fi network which requires a passcode for access, a passcode for the network can be stored in a memory associated with the medical equipment. For example, during an initial install or configuration of the medical equipment, the network passcode can be provided and stored in a memory associated with the medical equipment. When the medical equipment determines that a text message should be sent (e.g., upon deployment, upon completion of a self-test routine), the medical equipment can establish a connection with the secured wireless network by accessing stored passcode information for the secured wireless network. Thus, in some examples, the medical equipment can send and receive text messages via a secured wireless network.

Figure 1:
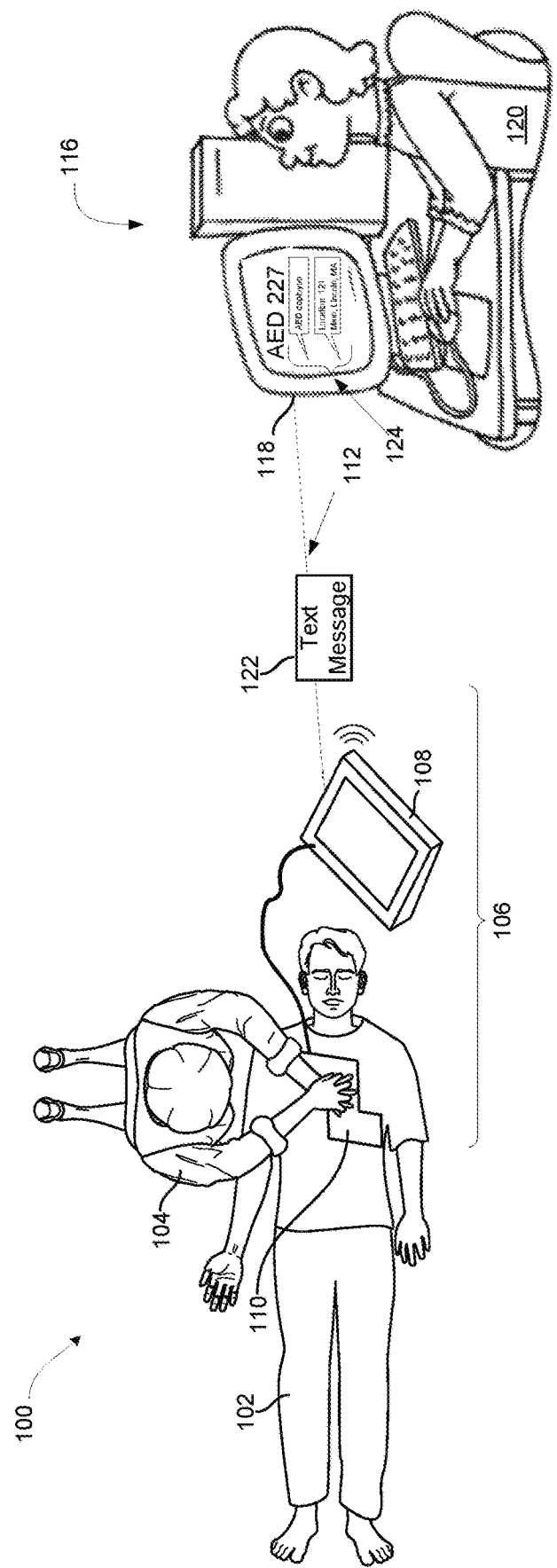
FIG. 1 is a schematic diagram of an exemplary system for responding to an emergency medical condition.

Referring to FIG. 1, at a rescue scene 100, a caregiver 104 performs cardiopulmonary resuscitation (CPR) on a subject 102. An electronic defibrillating system 106 including a defibrillator, such as an automated external defibrillator (AED) 108, a professional defibrillator, or another type of defibrillating apparatus, instructs the caregiver 104 in performing CPR and provides defibrillation as needed via external electrode pads 110. The subject may be, for instance, an individual who has apparently undergone sudden cardiac arrest. The caregiver 104 may be, for instance, a civilian responder with limited or no training in lifesaving techniques; a first responder, such as an emergency medical technician (EMT), police officer, or firefighter; or a medical professional, such as a physician or nurse. The caregiver 104 may be acting alone or may be acting with assistance from one or more other caregivers, such as a partner EMT.

The defibrillating system 106 is connected via a communication channel 112 to an emergency response center 116, such as a 911 call center, a police dispatch, an ambulance dispatch, a fire department, or another emergency response center. In some examples, the communication channel 112 can be a short-range wireless communication channel, such as a Bluetooth or WiFi connection, that is connected to a hardwired communication channel. The communication channel 112 can support the delivery of text messages 122 between the defibrillating system 106 and the emergency response center 116. The text messages from the defibrillating system 106 are displayed on a display 118 (e.g., a computer monitor, television, mobile communication device, or other display) at the emergency response center 116 (e.g., displayed messages 124), enabling a responder 120 (e.g., a dispatcher) to receive information from the defibrillating system 106. In some embodiments, the defibrillating system 106 can send information about its deployment state such as when the device is turned on or when the device delivers a defibrillation shock. In some additional embodiments, the defibrillating system 106 can also monitor the subject 102 during treatment and transmit real-time subject monitoring data to the emergency response center 116 via text message.

In some examples, the defibrillating system 106 can send a text message to the emergency response 116 center automatically upon the occurrence of certain events, such as deployment of the defibrillating system 106. Additionally, in some examples, the defibrillating system 106 can send user generated text messages such as messages input by caregiver 104 and display text messages received from the emergency response center 116 on a display unit of the defibrillating system 106, or in associated device.

Figure 2A:
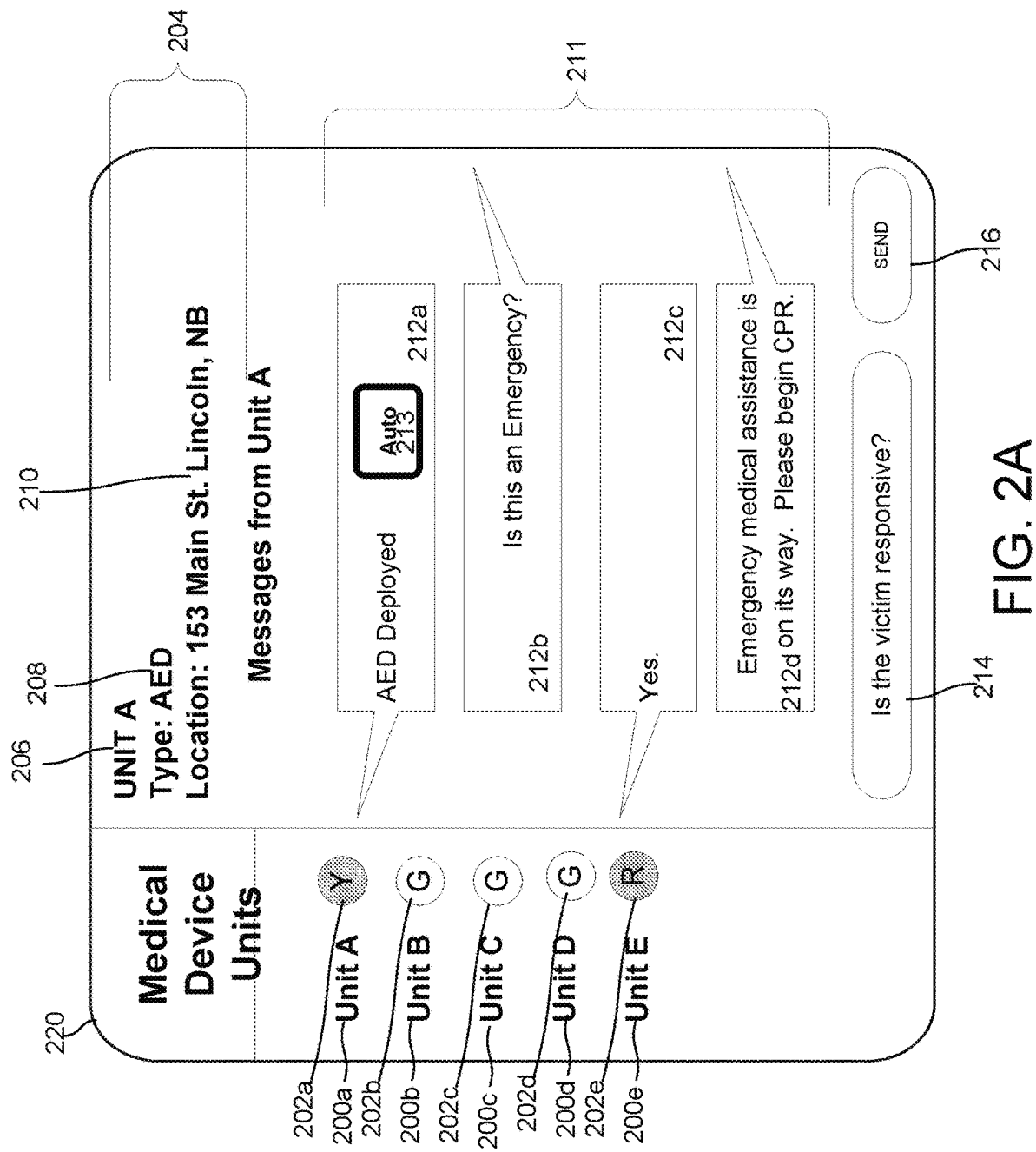
FIGS. 2A, 2B, and 2C are exemplary screen shots for displaying text-based updates from medical equipment.

FIG. 2A shows an exemplary user interface 220 at the emergency response center 116 that includes communications between the defibrillating system 106 and an individual 120 at the emergency response center. User interface 220 includes a portion 211 configured to display text messages between the defibrillating system 106 and the emergency response center 116. In the example of FIG. 2, these messages include both auto generated messages from the defibrillating system 106 such as message 212a that is sent from the defibrillating system 106 upon activation of the defibrillating system 106 and user generated messages sent from the defibrillating system 106 such as message 212c. Auto-generated messages (e.g., messages automatically generated and sent by the defibrillator) can be displayed with visual indicia 213 that indicates that the message was automatically sent. The messages in portion 211 also include messages sent from an individual at the emergency response center to the defibrillating system 106 such as messages 212b and 212d. Thus, text-based communications are provided between the defibrillating system 106 and the emergency response center. User interface 220 also includes a message input box 214, and a control 216 for sending the message to the medical device unit.

User interface 220 also includes a portion 204 that displays information about the defibrillating system 106, which is sending and receiving the messages displayed in portion 211. This information can include a unit name 206, a unit type 208 which identifies the make and model of the defibrillating system 106, and a location 210. The location can be a location determined by accessing a stored database of location information, a location provided by the defibrillating system 106 based on information stored in the defibrillating system 106, or a location provided by the defibrillating system 106 unit based on GPS location data.

User interface 220 also includes a control area for selecting different defibrillating systems. Selection of a different system displays communications between the selected defibrillating system and the emergency response center in area 211. The control area can include a unit identifier such as unit identifiers 200a-e and a status indicator such as status indicators 202a-e. The status indicators can indicate when a text message has been received from the associated the defibrillating system. The status indicators can be displayed as color-coded icons associated with each piece of medical equipment where the color coding is indicative of the status. For example as shown in FIG. 2A, the entries in the status column can be color-coded to indicate whether a new/unread message has been received from the associated defibrillating system. In one particular example, a red color coding of the icon could be representative of equipment for which a new text message that is the first text message in a conversation has been received, a yellow color coding can be representative of equipment for which a new message has been received in an ongoing series of text messages, and a green color coding could be representative of equipment for which no text messages have been received within a particular time period. In the particular example shown in FIG. 2A, device 200a has a status indicator 202a indicating that a new message has been received in an ongoing conversation and device 200e has a status indicator 202e indicating that a new message has been received which is the first message in a new conversation.

Figure 2B:
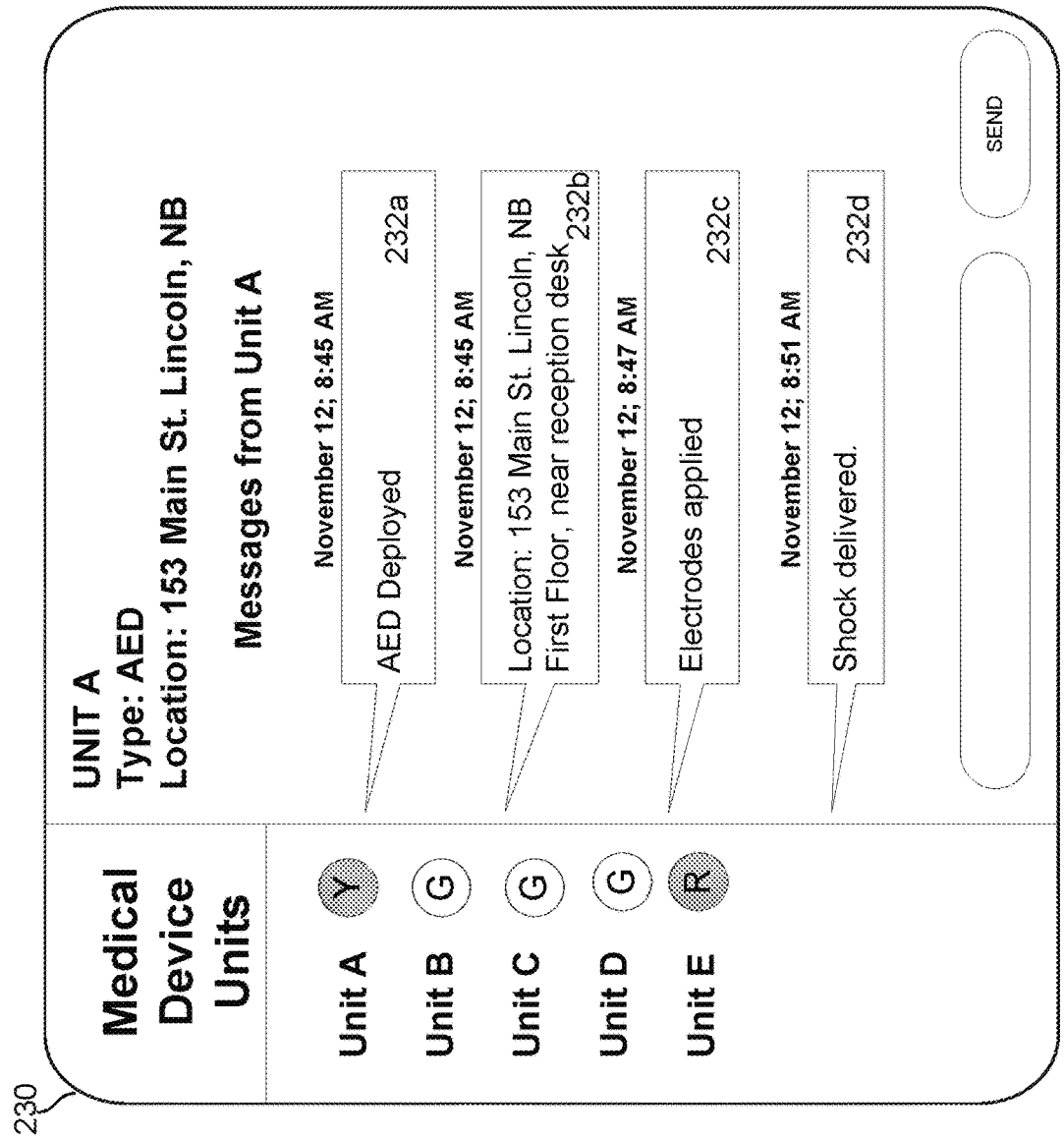

In some examples, as shown in FIG. 2B, a defibrillation device such as a defibrillation unit 106 in FIG. 1 can provide automatically generated text messages (e.g., messages 232a-d) to the emergency response center (or to another device such as a handheld device or a mobile phone used by an EMT or computing device in an ambulance). These messages can be automatically generated based on the occurrence of certain events on defibrillation unit. For example, messages can include a deployment message 232a sent to the emergency response center when the defibrillation unit is deployed, an application message 232c sent when electrodes have been applied, a defibrillation message 232d sent when a defibrillation shock has been administered, or upon other occurrences. Additionally, the automatically generated messages can include a location message 232b that provides a current location for the defibrillation unit sending the text message. Such messages can allow the emergency response center to be informed of the status of an ongoing rescue without requiring the rescuer to interrupt his or her administration of CPR or performance of other activities. Additionally, automatic generation and transmission of a text message upon deployment of medical equipment such as a defibrillation unit can reduce the time between when a rescue begins and when the emergency response center is notified. For example, rather than notification to the emergency response center occurring upon the rescuer initiating a 911 call, such notification can automatically occur whenever the defibrillation unit is deployed.

Figure 2C:
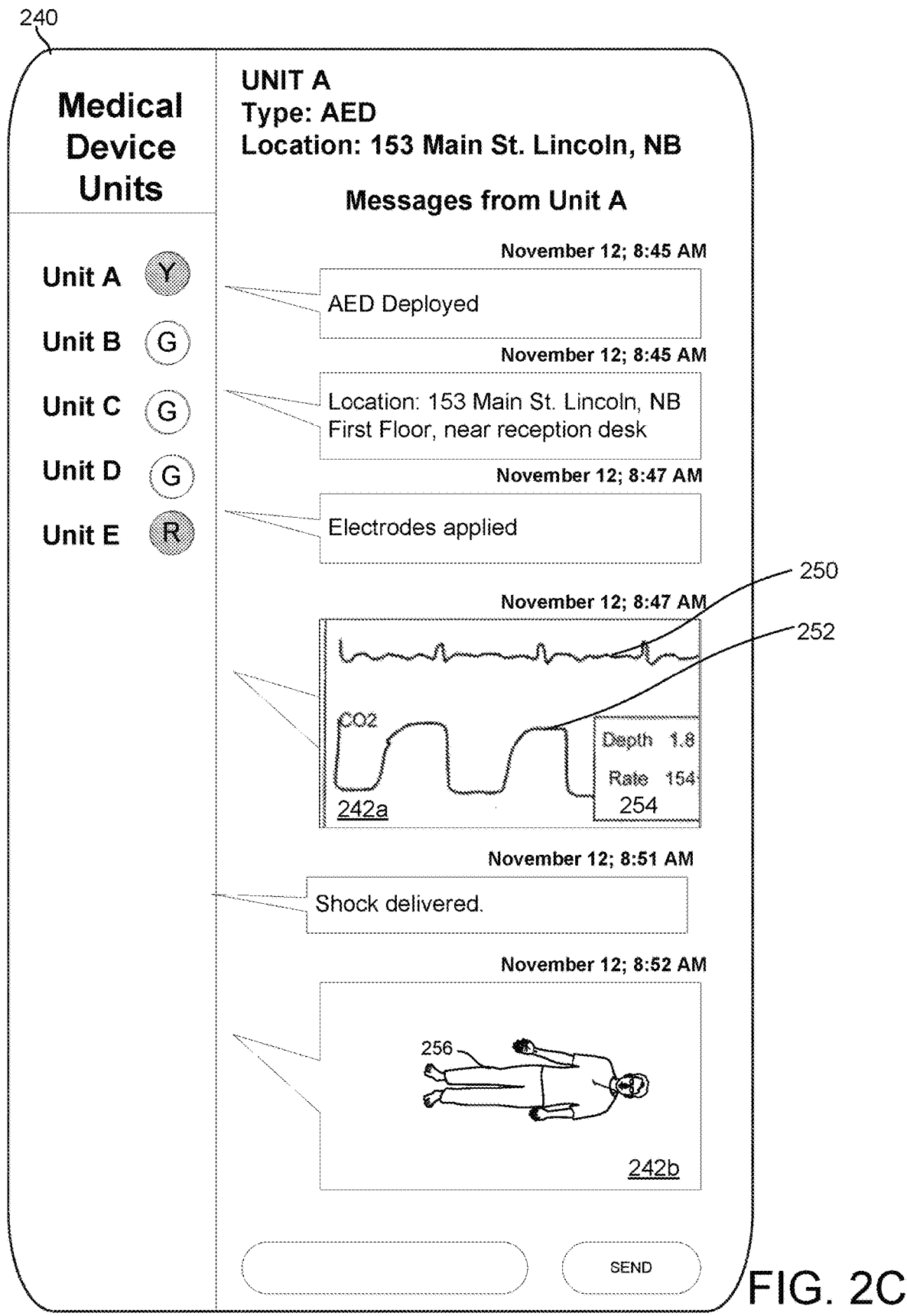

In some examples, the defibrillating system 106 can additionally monitor the subject 102 during treatment and collect real-time subject monitoring data. As shown in FIG. 2C, this monitoring data can be transmitted to the emergency response center via text message either as a screen capture using a MMS message (e.g., as shown in message 242a) or as text-based information (not shown). For instance, signals such as an ECG waveform (e.g., signal 250), an $SpO_2$ level, a blood pressure, $CO_2$ (e.g., signal 252), a measure of cardiac output, or a measure of heart rate may be monitored and summary information can be sent to the emergency response center via text message. Alternatively or additionally, compression parameters, such as a sternal motion signal, a compression rate, a compression depth, or another measurement of compression, may be monitored and sent to the emergency response center via text message (e.g., as shown in box 254). Some or all of these types of subject monitoring data may be transmitted from the defibrillation unit to the emergency response center 116 via text messages.

In some additional examples, as shown in FIG. 2C, the defibrillating system 106 and additionally include a camera (not shown) for capturing image information from the rescue scene. The captured image information can be sent to the emergency response center via text message. For example, a text message, such as message 242b can include a photograph 256 or other image information, such as video information, obtained by the camera associated with the defibrillating system. Providing such image information can be beneficial in allowing the emergency response center and/or a potential responder to remotely assess the situation, deploy the appropriate responders, and/or provide instructions to a rescuer.

Figure 3:
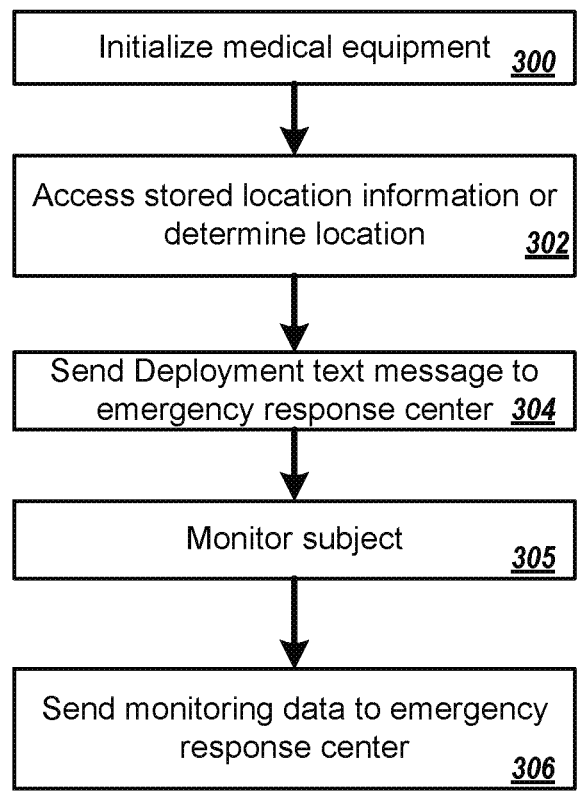
FIG. 3 is a flow chart of a process for sending text-based updates from medical equipment according to an example embodiment of the invention.

As noted above, in some examples, the defibrillation unit can provide location information automatically via text message (e.g., text message 232b in FIG. 2B). FIG. 3 shows an exemplary process for sending text-based updates from the defibrillation unit. The process begins with the initialization of the defibrillation unit (300). Upon initialization, the defibrillation unit accesses stored location information or determines the location of the defibrillation unit (302). For example, the location information can be stored in a memory associated with the defibrillation unit and accessed at the time of initialization. In another example, the defibrillation unit can include a GPS device which can be used to determine a current location for the defibrillation unit. The defibrillation unit sends a text message (e.g., an SMS or MMS message) to an emergency response center, indicating the defibrillation unit has been deployed (304). This text message includes information about the location of the defibrillation unit. In some additional examples, two separate text messages can be sent with a first indicating that the defibrillation unit has been deployed and a second indicating the current location of the defibrillation unit. The defibrillation unit monitors the subject during treatment and collects real-time subject monitoring data, such as the monitoring data described above (305). A subset of the monitored subject data is sent to the emergency response center in the form of a text message (306).

While the examples described above in relation to FIGS. 1-3 describe sending text messages between defibrillation units and an emergency response center, text messages can be sent from a variety of types of emergency medical equipment, such as medical monitors to the emergency response center.

While the examples described above in relation to FIGS. 1-3 describe sending text messages between emergency medical equipment such as AEDs and an emergency response center, text messages can be sent from emergency medical equipment to a variety of remotely located devices and systems. For example, the messages described above as being sent to the emergency response center could additionally or alternatively be sent to a mobile phone of a responder, such as an EMS responder, to a hospital, to a computing device located in an ambulance, or to other individuals who may be equipped to respond to the emergency situation.

In some additional examples, text messages can be used to assist in maintaining medical equipment such as defibrillation units. In order for a defibrillator to be useful during a medical emergency, the defibrillator must be charged and functional when the device is needed. In order to ensure the defibrillators are functional, regular servicing is needed. For example, batteries must be replaced when they no longer store adequate charge to power the defibrillator, electrodes may need to be replaced to ensure the electrodes will function appropriately, and the like. As such, after defibrillator is purchased and installed regular servicing is provided to ensure that the defibrillator will be available and functional when needed. In some examples, the defibrillation unit can send text messages to convey a status of the defibrillation unit. These messages can assist a user to provide servicing to the defibrillation units when needed. For example, if a battery in the defibrillation unit has a low level of charge, the defibrillation unit can send a text message to a servicing center and based on this text message, the servicing center can deploy an individual to replace the battery in the defibrillation unit.

Figure 4:
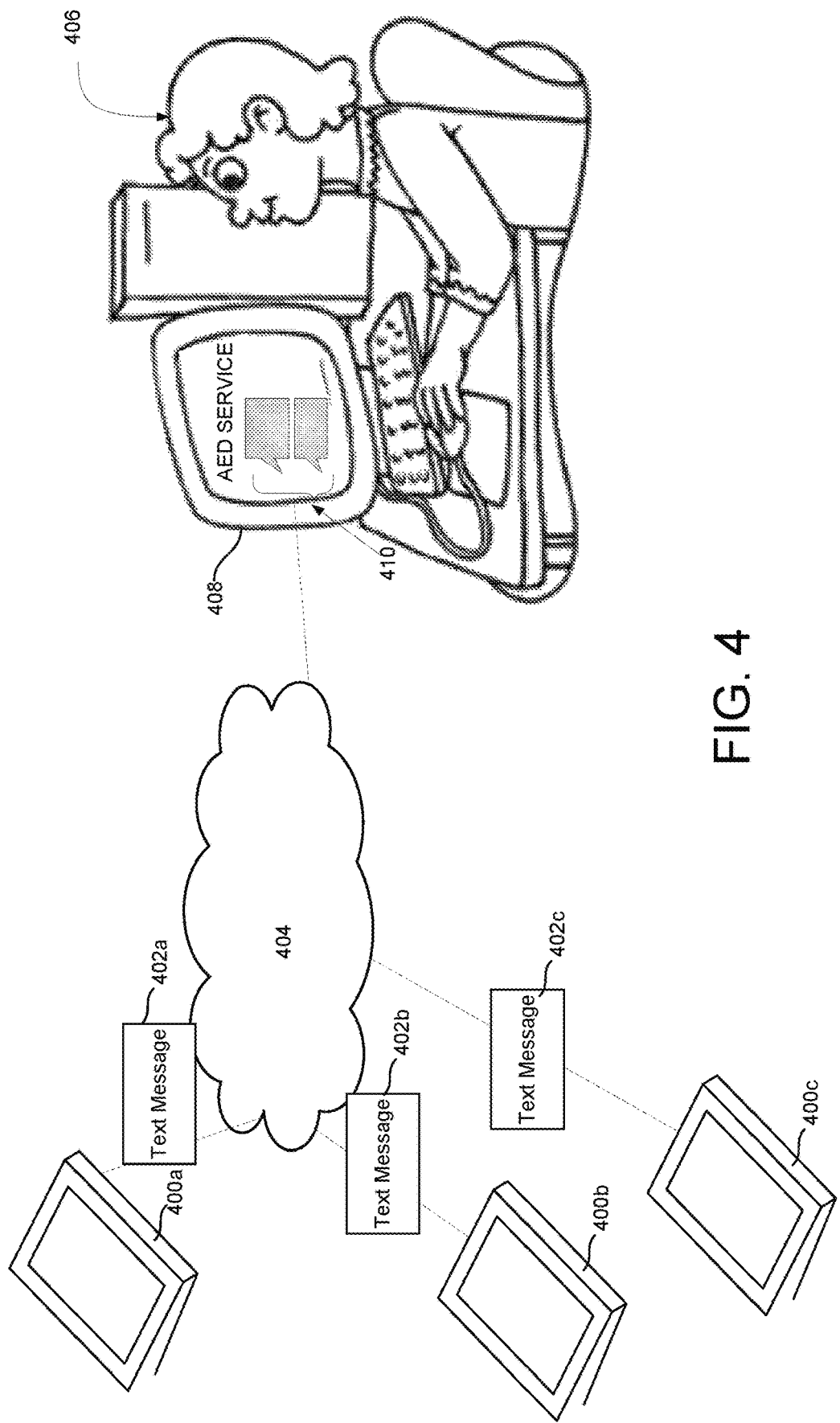
FIG. 4 is a schematic diagram of a system for managing medical equipment according to an example embodiment of the invention.

For example, as shown in FIG. 4, defibrillation units such as AEDs 400a, 400b, and 400c can send text messages (e.g., text messages 402a-c) to a service center 408. The text messages can be displayed on a user interface (e.g., as messages 410) for an individual 406 at the service center to review and take appropriate actions based on the received text messages. The text messages 402a-c can be sent to the service center 408 over the Internet 404 and/or over a cellular communication channel.

Figure 5:
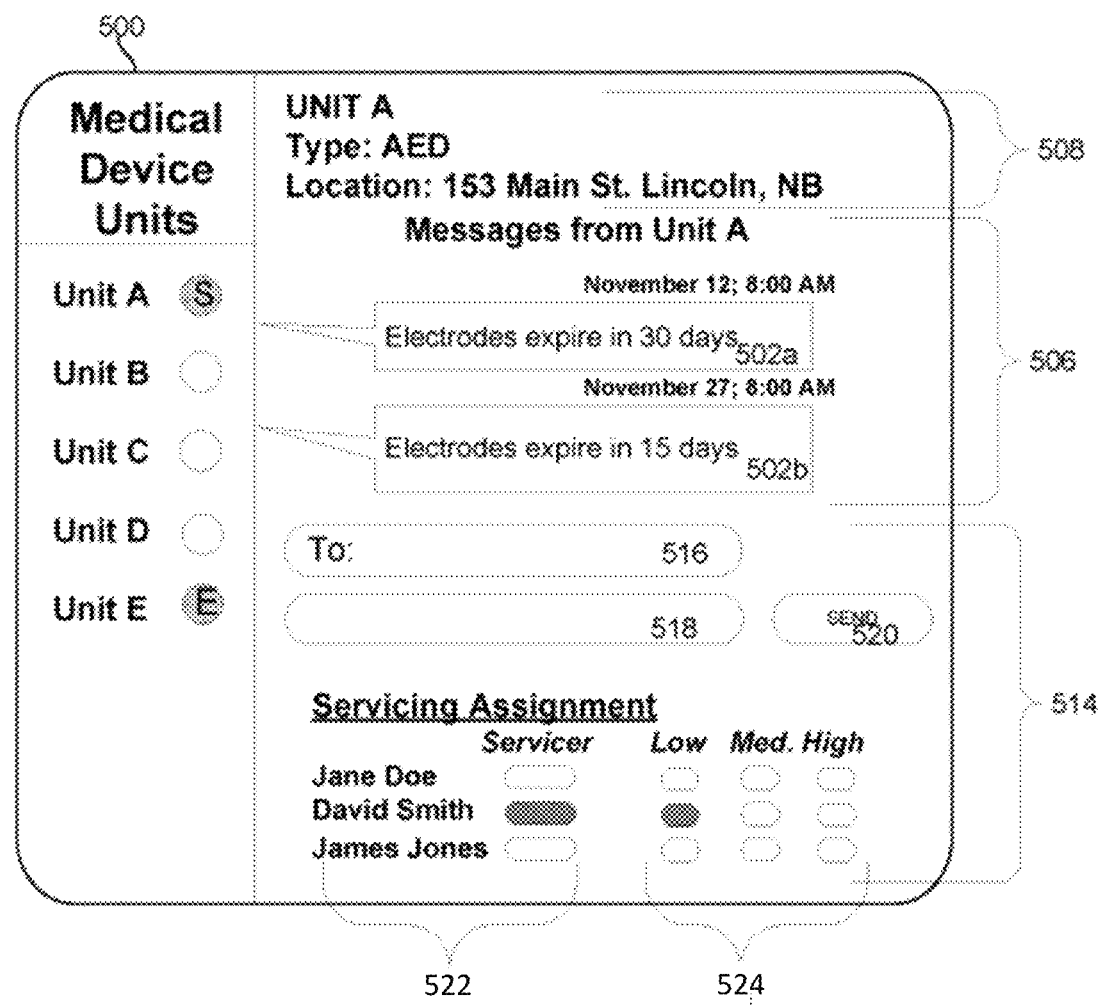
FIG. 5 is an exemplary screen shot for displaying text-based updates including status information for medical equipment.

FIG. 5 shows an exemplary screen shot for providing information about the status of defibrillation units to an administrator of the defibrillation units.

User interface 500 includes a portion 506 configured to display text messages between the defibrillation unit and an individual at the service center. These messages can include automatically generated messages from the defibrillation unit such as messages that convey status information about the defibrillation unit.

User interface 500 also includes a message assignment and forwarding portion 514. The message assignment and forwarding portion 514 enables a user at the service center to forward the text message from the defibrillation unit to another individual and/or to assign servicing to a particular individual. For example, upon receipt of the text message from a particular defibrillation unit, a user could forward the text message to another individual such that that individual could perform the needed servicing. The user at the service center could forward the message by entering an identifier/username for the individual to forward the message to in box 516, and optionally entering an additional message in box 518. The message from the defibrillator and the additional message from the user at the service center (if provided) can be forwarded to the individual identified in box 516 by selection of the send button 520.

In some additional examples, servicing can be assigned by selection of an individual from a list of individuals 522 available to perform the servicing. For example, a servicing company could maintain a list of individuals who perform needed servicing of the medical devices and particular tasks could be assigned to those individuals by selecting the individual. Additionally, user interface 500 allows a user at the service center to assign urgency to the servicing by selecting and associated urgency box in section 524. In the example shown in user interface 500, the user at the service center has assigned servicing of the 'unit A' to David Smith by selecting the input associated with David Smith and assigned an urgency of "low" by selecting associated control. Upon making the selections, a message is sent to the selected individual providing information about the needed servicing.

User interface 500 also includes a portion 508 that displays information about the defibrillation unit, which is sending and receiving the messages displayed in portion 506. This information can include a unit name, a unit type which identifies the make and model of the defibrillation unit, and a location. The location can be a location determined by accessing a store database of location information, a location provided by the defibrillation unit based on information stored in the medical device unit, or a location provided by the defibrillation unit based on GPS location data.

User interface 500 also includes a control area for selecting defibrillation units. Selection of a different unit displays communications between the selected defibrillation unit and the service center in area 506. The control area can include a unit identifier such and a status indicator. The status indicators can indicate when a text message has been received from the associated defibrillation unit. The status indicators can be displayed as color-coded icons associated with each piece of medical equipment where the color coding is indicative of the status. For example as shown in FIG. 5, the entries in the status column can be color-coded to indicate whether a new/unread message has been received from the associated defibrillation unit. In one particular example, a red color coding of the icon could be representative of equipment for which a new text message indicating an error has been received, a yellow color coding can be representative of equipment for which a new message has been received indicating expiration of a component or other routine servicing is needed, and a green color coding could be representative of equipment for which no text messages have been received within a particular time period. In the particular example shown in FIG. 5, unit 'A' has a status indicator indicating that servicing is needed (e.g., that the electrodes will expire in 15 days) and unit 'E' has a status indicator indicating that an error message has been received.

In some examples, a defibrillator can include a self-test unit configured to perform self-tests at regular time-based intervals. The results of the self-test can be sent to the servicing center via text message. Thus, if a problem is identified by the self-test, details are provided to the servicing center. Further, because self-tests are scheduled to occur at regular time intervals, the servicing center can identify failures in devices based on the lack of an expected message. For example, if a defibrillation unit is scheduled to perform a self-test monthly, and the results are not received, then the servicing center can identify the defibrillation unit as potentially having a problem that is prohibiting performance of the self-test (e.g., a battery with inadequate charge).

While the examples described above in relation to FIGS. 4-5 describe sending text messages between defibrillation units and a service center, text messages can be sent from a variety of types of medical equipment, such as medical monitor equipment to the service center.

A number of embodiments have been described. Nevertheless, it will be understood that various modifications may be made without departing from the spirit and scope of the invention. For example, much of this document has been described with respect to defibrillation units, but other types of devices may be employed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims. Many other implementations of the invention other than those described above are within the invention, which is defined by the following claims.

What is claimed is:

1. A medical device management system, the system comprising:
   a defibrillating apparatus comprising:
   a plurality of electrodes configured to monitor ECG signals of a patient and deliver a defibrillation shock to the patient, and
   a communication unit configured to:
   establish a secured wireless network connection that requires a network passcode to gain access to the secured wireless network,
   receive a signal indicative of deployment of the defibrillating apparatus to the patient,
   automatically generate a first text message upon receipt of the signal indicative of deployment of the defibrillating apparatus,
   associate the first text message with a unit identifier specific to the defibrillating apparatus,
   automatically send, via the secured wireless network connection, the first text message to a mobile handheld device associated with a caregiver,
   automatically generate a second text message comprising defibrillation shock status upon delivery of the defibrillation shock,
   associate the second text message with the unit identifier specific to the defibrillating apparatus, automatically send, via the secured wireless network connection, the second text message to the mobile handheld device associated with the caregiver; and the mobile handheld device associated with the caregiver comprising a user interface comprising a display configured to display a plurality of displayed unit identifiers, each of the plurality of displayed unit identifiers being associated with a particular defibrillating system of a plurality of defibrillating systems, wherein the mobile handheld device is configured to:

receive a user selection of a defibrillating system of the plurality of defibrillating systems for display of communication information between the selected defibrillating system and the mobile handheld device, wherein the selected defibrillating system comprises the defibrillating apparatus, receive the first text message and associate the first text message with the defibrillating apparatus based on the unit identifier specific to the defibrillating apparatus, and display the first text message on the display, receive the second text message and associate the second text message with the defibrillating apparatus based on the unit identifier specific to the defibrillating apparatus, and display the second text message on the display, in response to the received second text message, send a third text message to be received by the defibrillating apparatus, the third text message including patient treatment information;

wherein the defibrillating apparatus is configured to receive the third text message including the patient treatment information from the mobile handheld device and to display the third text message on the display, wherein the display comprises, for each of the plurality of displayed unit identifiers, an associated status indicator that indicates when a text message has been received from the defibrillating system, of the plurality of defibrillating systems, associated with the associated status indicator, wherein the associated status indicator comprises a color-coded icon that indicates a particular communication status of a plurality of communication statuses, the plurality of communication statuses comprising: a first status indicating that no text message has been received, a second status indicating that an initial text message has been received, and a third status indicating that a second or later message has been received.

2. The system of claim 1, wherein the handheld device is a mobile phone of the caregiver.

3. The system of claim 1, further comprising an emergency response center configured to receive one or more text messages from the communication unit of the defibrillating apparatus.

4. The system of claim 3, wherein the communication unit is configured to automatically send, via the secured wireless network connection, the first text message to the emergency response center.

5. The system of claim 4, wherein the emergency response center is configured to receive the first text message and provide instructions input by an individual at the emergency response center based on the received first text message to the communication unit of the defibrillating apparatus.

6. The system of claim 3, wherein the emergency response center is configured to receive the first text message and send instructions for the caregiver input by an individual at the emergency response center based on the received one or more text messages.

7. The system of claim 3, wherein the communication unit is configured to automatically send, via the secured wireless network connection, the second text message to the emergency response center.

8. The system of claim 7, wherein the emergency response center is configured to receive the second text message and provide instructions input by an individual at the emergency response center based on the received second text message to the communication unit of the defibrillating apparatus.

9. The system of claim 3, wherein the emergency response center is configured to receive the second text message and send instructions for the caregiver input by an individual at the emergency response center based on the received text messages.

10. The system of claim 3, wherein the emergency response center includes one or more of: a 911 call center, a police dispatch center, a fire dispatch center, a computing device in an ambulance, and a hospital.

11. The system of claim 1, wherein the communication unit is configured to send periodic text messages regarding a status of the defibrillating apparatus at predetermined intervals.

12. The system of claim 1, wherein the defibrillating apparatus further includes a global positioning unit configured to generate GPS location data associated with the defibrillating apparatus.

13. The system of claim 12, wherein the communication unit is configured to send one or more text messages to the handheld device with the GPS location data associated with the defibrillating apparatus.

14. The system of claim 1, wherein the unit identifier includes at least one of: a defibrillator type, a make of the defibrillating apparatus, and a model of the defibrillating apparatus.

15. The system of claim 1, wherein the defibrillating apparatus is configured to monitor the patient in real time obtains one or more of: an electrocardiogram (ECG) waveform, an Sp02 level, a blood pressure, CO2 level, a measure of cardiac output of the patient, and a measure of a heart rate.

16. The system of claim 1, wherein the defibrillating apparatus includes a camera configured to capture image data and/or video data, and wherein the communication unit is configured to send one or more text messages and/or one or more multimedia messages with the captured image data and/or video data.

17. The system of claim 1, wherein the defibrillating apparatus is an automated external defibrillator.

18. The system of claim 1, wherein the defibrillating apparatus is a professional defibrillator.

19. The system of claim 1, wherein the handheld device is configured to connect with the defibrillating apparatus via a short-range wireless connection or a remote wireless connection.

20. The system of claim 1, wherein a second device, which is separate from the defibrillating apparatus and the handheld device, comprises the user interface display, and wherein the defibrillating apparatus is further configured to display the third text message on the user interface display of the second device.

21. A medical device management system, the system comprising:
a defibrillating apparatus comprising:
a plurality of electrodes configured to monitor ECG signals of a patient and deliver a defibrillation shock to the patient, and
a communication unit configured to:
receive a signal indicative of deployment of the defibrillating apparatus to the patient,
automatically generate a first text message upon receipt of the signal indicative of deployment of the defibrillating apparatus,
associate the first text message with a unit identifier specific to the defibrillating apparatus,
automatically send the first text message to a mobile handheld device associated with a caregiver,
automatically generate a second text message comprising defibrillation shock status upon delivery of the defibrillation shock,
associate the second text message with the unit identifier specific to the defibrillating apparatus,
automatically send the second text message to a mobile handheld device associated with a caregiver; and
the mobile handheld device associated with the caregiver comprising a user interface comprising a display configured to display a plurality of displayed unit identifiers, each of the plurality of displayed unit identifiers being associated with a particular defibrillating system of a plurality of defibrillating systems, wherein the mobile handheld device is configured to:
receive a user selection of a defibrillating system of the plurality of defibrillating systems for display of communication information between the selected defibrillating system and the mobile handheld device, wherein the selected defibrillating system comprises the defibrillating apparatus,
receive the first text message and associate the first text message with the defibrillating apparatus based on the unit identifier specific to the defibrillating apparatus, and display the first text message on the display,
receive the second text message and associate the second text message with the defibrillating apparatus based on the unit identifier specific to the defibrillating apparatus, and display the second text message on the display,
in response to the received second text message, send a third text message to be received by the defibrillating apparatus, the third text message including patient treatment information;

wherein the defibrillating apparatus is configured to receive the third text message including the patient treatment information from the mobile handheld device and to display the third text message on the display,
wherein the display comprises, for each of the plurality of displayed unit identifiers, an associated status indicator that indicates when a text message has been received from the defibrillating system, of the plurality of defibrillating systems, associated with the associated status indicator, wherein the associated status indicator comprises a color-coded icon that indicates a particular communication status of a plurality of communication statuses, the plurality of communication statuses comprising: a first status indicating that no text message has been received, a second status indicating that an initial text message has been received, and a third status indicating that a second or later message has been received.

22. The system of claim 21, further comprising an emergency response center configured to receive one or more text messages from the communication unit of the defibrillating apparatus.

23. The system of claim 22, wherein the emergency response center includes one or more of: a 911 call center, a police dispatch center, a fire dispatch center, a computing device in an ambulance, and a hospital.

24. The system of claim 21, wherein the defibrillating apparatus further includes a global positioning unit configured to generate GPS location data associated with the defibrillating apparatus.

25. The system of claim 24, wherein the communication unit is configured to send one or more text messages to the handheld device with the GPS location data associated with the defibrillating apparatus.

26. The system of claim 21, wherein the unit identifier includes at least one of: a defibrillator type, a make of the defibrillating apparatus, and a model of the defibrillating apparatus.

27. The system of claim 21, wherein the handheld device is configured to connect with the defibrillating apparatus via a short-range wireless connection or a remote wireless connection.

28. The system of claim 21, wherein a second device, which is separate from the defibrillating apparatus and the handheld device, comprises the user interface display, and wherein the defibrillating apparatus is further configured to display the third text message on the user interface display of the second device.

* * * * *